(12) United States Patent
Bates et al.

(10) Patent No.: US 7,088,447 B1
(45) Date of Patent: Aug. 8, 2006

(54) PARTICLE COUNTER WITH SELF-CONCEALING APERTURE ASSEMBLY

(75) Inventors: Thomas Bates, Westminster, CO (US); Richard O. Miller, Loveland, CO (US); Richard A. Alexander, Berthoud, CO (US)

(73) Assignee: Particle Measuring Systems, Inc., Boulder, CO (US)

( * ) Notice: Subject to any disclaimer, the term of this patent is extended or adjusted under 35 U.S.C. 154(b) by 0 days.

(21) Appl. No.: 11/141,453

(22) Filed: May 31, 2005

Related U.S. Application Data

(60) Provisional application No. 60/657,626, filed on Mar. 1, 2005.

(51) Int. Cl.
*G01N 21/00* (2006.01)
(52) U.S. Cl. .................................... 356/338
(58) Field of Classification Search ............. None
See application file for complete search history.

(56) References Cited

U.S. PATENT DOCUMENTS

| | | | | | |
|---|---|---|---|---|---|
| 4,226,532 | A | * | 10/1980 | Berber et al. | 356/336 |
| 5,085,500 | A | * | 2/1992 | Blesener | 356/338 |
| 5,872,627 | A | * | 2/1999 | Miers | 356/338 |

* cited by examiner

*Primary Examiner*—Tu T. Nguyen
(74) *Attorney, Agent, or Firm*—Patton Boggs

(57) ABSTRACT

A particle measurement system using a single component light collecting system with an aperture having a portion within direct view of the light detector. An aperture assembly extending into a sample may be self-concealing by having an extended portion to block light from directly illuminating the light detector. Alternatively, a smooth, reflective inside surface of the aperture assembly provides for self-concealment by causing spontaneous emitted light to have low angles of reflection. In either case, spontaneously emitted light is substantially prevented from reflecting directly into the light detector, thereby reducing light noise to the level of molecular noise.

21 Claims, 3 Drawing Sheets

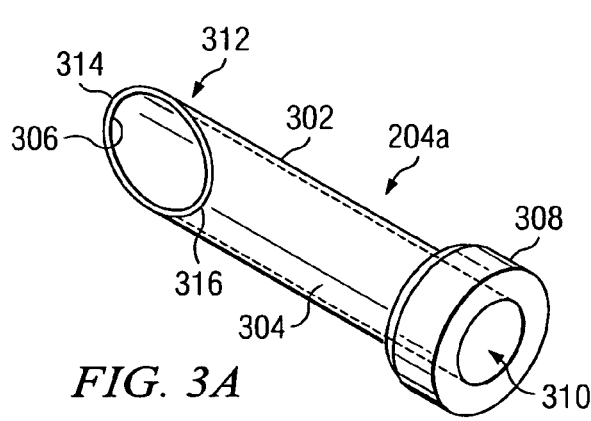
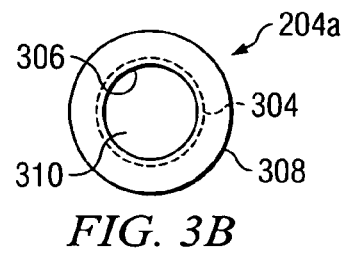
*FIG. 3B*
*FIG. 3A*
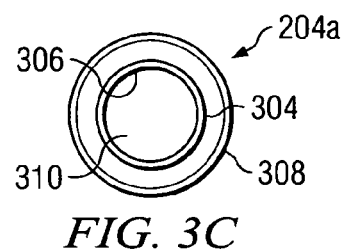
*FIG. 3C*
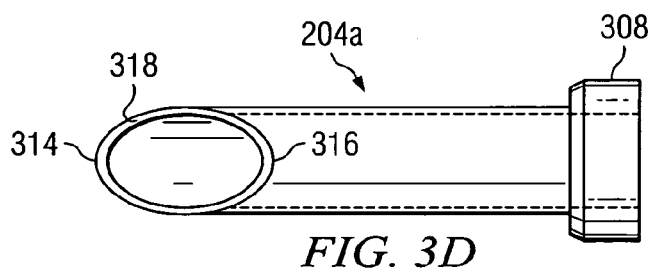
*FIG. 3D*
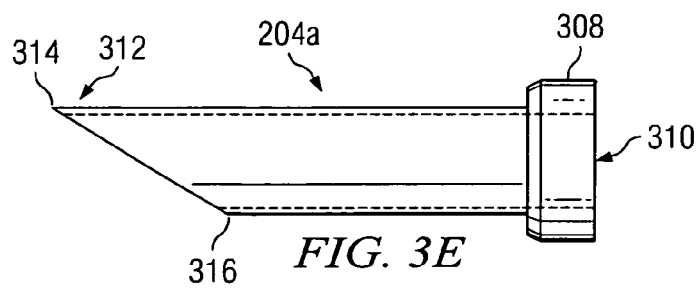
*FIG. 3E*

PARTICLE COUNTER WITH SELF-CONCEALING APERTURE ASSEMBLY

RELATED APPLICATION

This application claim benefit of U.S. Provisional Application No. 60/657,626 filed Mar. 1, 2005.

BACKGROUND OF THE INVENTION

1. Field of the Invention

The principles of the present invention are directed to a particle measurement system, and more particularly, but not by way of limitation, to a particle sensor having a single component collecting system.

2. Description of Related Art

Most people are familiar with the sight of dust in a sunbeam. Four things that are necessary for this include: sunlight (to illuminate the dust), dust (to reflect the sunlight), air (to carry the dust), and a person's eye (to see the dust, or more specifically to see the light reflected by the dust). An optical particle counter uses the same principles, but refines them to maximize its effectiveness. In modern particle counters, a laser light source is typically used, the sample (e.g., air) is controlled, and a high sensitivity photo or light detector is utilized to detect light that particles scatter. Typical uses of an optical particle counter include clean rooms, hospitals, and other facilities where cleanliness is important.

It is important to distinguish the science of particle counting from other scientific fields, such as photometry and cytometry, which also utilize scattered light, but in which the density of the particles in the fluid is relatively large; often it is the particles of the fluid itself that are detected and analyzed. These latter systems rely on collecting scattered light from thousands, millions, and even billions of particles; therefore, their principles of operation are very different from the principles used in particle counters, which detect individual particles suspended in a fluid.

As understood in the art, particle counters do not directly count particles, but rather count flashes of light scattered by particles (or shadows cast by backlit particles). Also, particle counters do not count every particle in a system of interest, but rather generate a statistically valid sample representative of the number of particles for average fluid in the rest of the system.

A large portion of the aerosol micro-contamination market having 0.3 micrometer (μm) to 0.5 μm sensitivity, 0.1 cubic feet per minute (CFM) to 1.0 CFM sample flow rate, use low cost particle sensors for determining particle counts. These sensors generally utilize a low power laser diode, typically 25–50 milliwatts (mW), a PIN photo-diode, and a single component light collecting system, which typically includes a surface spherical mirror. A single component collecting system is generally utilized to minimize system size and cost. While a single component collecting system cannot achieve the image blur-size capabilities of a multi-component solution, it is capable of collecting light at a relatively broad collection angle, typically +/−50° to 60°, and directing light onto a light detector. The image plane typically includes a photo-diode or other light detector. Magnification of a single component collecting system is generally slightly larger than 1×. One limitation of the single component collecting system is the inherent inability to effectively reduce optical noise known as the scattered light noise floor of the system.

Unlike multiple component collecting systems that have the ability to remove the laser aperture assembly from direct view of the photo-diode, a single component system has limited options when dealing with scattered light. All conventional particle measurement systems utilizing a single component collecting system include an aperture assembly that is in direct view of the system light detector. FIG. 1 is a schematic illustrating an exemplary particle measurement system 100 that includes a single component light collecting system 102. The particle measurement system 100 includes a housing 104 that houses the single component light collecting system 102 and electronics (not shown) used to count the number of particles detected by the single component light collecting system 102. The single component light collecting system 102 includes a sample chamber 106 composed of a frame 108, which maybe formed of multiple members. The frame 108 may define multiple apertures 110, 112, and 114. A pair of the apertures 110 and 112 may be configured in opposing relation. A laser diode module 116 including a laser diode (not shown) may be coupled to the frame 108 or another structural component located in the housing 104 and be positionally aligned to direct a light beam 118 into the sample chamber 106 via aperture 110. In the case of using a laser diode, the light beam 118 is a laser beam. Alternatively, if the light source is a non-lasing light source, then the light beam 118 is not a laser beam.

An aperture assembly 120 is typically configured as an aperture tube 119 that engages the aperture 110. The aperture assembly 120 is utilized to collimate the light beam 118 to minimize divergence of the light beam in the sample chamber so as to reduce optical noise. A beam stop 122 may be coupled to the frame 108 in optical alignment with the aperture 112. The beam stop 122 functions to absorb laser light that has exited the sample chamber 106.

An inlet orifice 124 may be coupled to the frame 108 and be utilized to flow air into the sample chamber 106 and through the light beam 118. A collecting mirror 126 or other reflecting device may be coupled to the frame 108 on a first side relative to the light beam 118. A light detector 128 may be disposed in relation to the aperture 114. In one embodiment, the light detector 128 is a photo diode. More specifically, the light detector may be a PIN photo diode. The light detector 128 may be coupled to the frame 108 or another member in the housing 104. Detector 128 is electrically coupled to a signal processor/amplifier 129. The signal processor/amplifier produces a system output signal on output 131.

In operation, the laser diode module 116 generates a light beam 118 that passes into the sample chamber 106 via the aperture assembly 120, and the sample chamber 106, through the aperture 112, and into the beam stop 122. The inlet orifice 124 flows air to be sampled through the light beam 118, such that particles in the air reflect light from the light beam 118 either directly into the light detector 128 or into the collecting mirror 126. The collecting mirror 126, which may be spherically shaped to focus light onto the light detector 128, reflects the light into the light detector for measurement thereby. In response to incident light, the light detector 128 generates an output signal, preferably a voltage pulse, characteristic of one or more parameters of the particles, as the size of the particles. The detector output signal is processed and/or amplified by signal processor/amp 129 to produce an output signal on output 131 that is characteristic of one or more parameters of the particles, such as size and number of particles in a size range.

Scattered light is generally caused by spontaneous emission of light from a facet (not shown) of the laser diode module 116. Laser light generated from the facet is considered to be stimulated emission light and is coherent. The stimulated emission light is predictable and is shaped and imaged by lenses of the laser diode module 116. The spontaneous emission light generated by the facet is not coherent and cannot be successfully shaped and imaged by lenses of the laser diode module 116. This spontaneous emission light causes a fairly broad light pattern that is centered on the more tightly focused primary laser beam. The unwanted spontaneous emission light pattern may reach over one percent of the power level of the light beam 118.

Collected light energy from a 0.3 micrometer particle may be as small as 0.000,015 percent of the power level of the light beam 118. In such a system, the unwanted spontaneous emission light pattern represents over 60,000 times the light level of the particle of interest, and therefore, is to be minimized and controlled. All conventional particle sensors or particle measuring systems utilize either an aperture tube, one or more apertures, or a combination of both to minimize the spontaneous emission light that is allowed to enter the sample chamber 106 of the particle measurement system 100.

The aperture assembly 120 attempts to prevent as much spontaneous emission light as possible from entering the sample chamber 106. The remaining portion of this spontaneous emission light that cannot be blocked is then collimated as well as possible by the aperture assembly 120. Ideally, this somewhat collimated light is then funneled through the optics chamber while minimizing the amount of light that diverges enough to come in contact with any physical structure of the sample chamber 106. Any light that diverges enough to contact the physical structure of the sample chamber 106 then scatters light energy that could be detected by the light detector 128. To minimize the amount of divergence, the aperture assembly 120 is sized to be as close to the viewed sample volume (e.g., air injected into the sample chamber 106) as possible. This inherently places the aperture assembly 120 in direct view of the light detector 128. Unfortunately, the aperture assembly 120 inherently produces unwanted diffraction and reflection light patterns of their own due to the spontaneous emission light reflecting off of an inside surface of the aperture assembly 120.

Once spontaneous emission light enters the sample chamber 106 and is detected by the light detector 128, it is referred to as scattered light noise. The fundamental noise limit of conventional single component particle measurement systems is scattered light noise. As shown in FIG. 1, the light detector 128 has a direct view of the aperture assembly 120 within the view angle 130, shown as dashed lines.

Conventional single component particle measurement systems have been designed to reduce the scattered light noise in a number of ways, including by making the inside of the aperture assembly 120 and sample chamber 106 light absorbing. In doing so, the surfaces of the aperture assembly 120 and sample chamber 106 are bead blasted and then either anodized or painted with a flat black paint. This bead blasting and flat black paint treatment causes the surfaces to appear multi-dimensional to the spontaneous emission light and very absorbing by scattering the light off of the peaks and valleys of the surfaces, and thus hitting the surfaces many times to have a better chance of being absorbed and not detected.

However, even by treating the inner surfaces of the aperture assembly 120 and sample chamber 106, complete elimination of the scattered light noise is not possible so that power from the laser diode module is increased to raise the signal-to-noise ratio. The signal-to-noise ratio goes up as the square root of the laser power, so by using a more powerful laser, the signal-to-noise ratio is increased. Another technique used to reduce the scattered light noise includes using a light dam around the photo diode. While the light dam eliminates some of the scattered light noise, it blocks some light from the particles in the light beam 118, thereby requiring more power to drive the laser diode to overcome the blockage. This increased power causes the laser diode to have a shorter lifespan, which is ultimately more costly for the manufacturer of the particle measurement system 100. The use of these techniques, even combined, still results in the scattered light noise being the primary noise factor in the optical system of the particle measurement system 100.

SUMMARY OF THE INVENTION

To reduce scattered light noise of a particle measurement system or particle counter, a self-concealing aperture is utilized. In one embodiment, an aperture assembly may be self-concealing by having at least a portion of the aperture assembly operate as a beam stop extending into a sample chamber. In a second embodiment, the aperture assembly may have a smooth, reflective inside surface of the aperture assembly to provide for self-concealment. In the case of the aperture assembly having an extended portion to operate as the beam stop, light reflected from the inside surface of the aperture assembly is blocked from directly illuminating a light detector of the particle measurement system, thereby substantially eliminating scattered light noise. In the case of the inside surface being more reflective, such as by being mechanically ream finished, polished, or using black glossy paint, reflection of the spontaneous emission of light is substantially prevented from reflecting directly into the light detector because the reflection angles are reduced (i.e., the reflections are more horizontal), thereby substantially eliminating scattered light noise.

The invention provides a system for detecting individual particles suspended in a fluid, the system comprising: a housing having a sample chamber; a fluid inlet orifice directing a fluid flow into the sample chamber; a light source for producing and directing light into the sample chamber and through the fluid flow; a light detecting element producing an output signal characteristic of individual particles suspended in the fluid; an aperture assembly located to aperture the light, the aperture assembly having a portion in direct view of the light detecting element, the aperture assembly having an inside surface exposed to the light, a first end in the sample chamber, and a second end, the first end having a top edge and a bottom edge, the top edge extending further into the sample chamber than the bottom edge; and a light collector located to collect light scattered by particles in the fluid flow and direct the collected light to the light detecting element, the optical components of the light collector consisting essentially of a single optical component; wherein the aperture assembly is oriented such that the extended top edge is on the same side as the light detecting element and sufficiently long to optically block essentially all light reflecting from the inside surface of the aperture assembly from directly illuminating the light detector, thereby reducing optical noise in the system. Preferably, the extended top edge is positioned to optically block the reflecting light from the inside surface of the aperture assembly at or above a critical angle at which the light detector is capable of detecting light. Preferably, the extended top edge blocks sufficient light from the inside surface of the aperture assembly to reduce the optical noise in the system to the level of molecular noise. Preferably, the inside surface of the aperture assembly has a roughness of thirty-two micro-inches or less. Preferably, the inside surface of the aperture assembly has a roughness of eight micro-inches or less. Preferably, the light source is a laser diode operated at a power of 15 milliwatts or less.

In another aspect, the invention also provides a system for detecting individual particles suspended in a fluid, the system comprising: a housing having a sample chamber; a fluid inlet orifice directing a fluid flow into the sample chamber; a light source for producing and directing light into the sample chamber and through the fluid flow; a light detecting element producing an output signal characteristic of individual particles suspended in the fluid; an aperture assembly located to aperture the light, the aperture assembly having a portion in direct view of the light detecting element, the aperture assembly having an inside surface exposed to the light and a first end in the sample chamber; and a light collector located to collect light scattered by particles in the fluid flow and direct the collected light to the light detecting element; the optical components of the light collector consisting essentially of a single optical component; the inside surface of the aperture assembly configured to reflect light so that essentially none of the light reflected from the inside surface is capable of directly illuminating the light detector, thereby reducing optical noise in the system for detecting particles. Preferably, the inside surface of the aperture assembly has a mechanical ream finish. Preferably, the inside surface of the aperture assembly has a maximum roughness of thirty-two micro-inches or less. More preferably, the inside surface of the aperture assembly has a maximum roughness of twenty micro-inches or less. Most preferably, the inside surface of the aperture assembly has a maximum roughness of eight micro-inches or less. Preferably, the inside surface of the aperture assembly comprises a polymer. Preferably, the polymer is embedded with black colored particles. Preferably, the aperture assembly is covered with a glossy black paint. In another embodiment, the inside surface of the aperture assembly is molded using a polished mold. Preferably, the aperture assembly has a length at least twice as long as the diameter of the aperture opening. Preferably, the light source is a laser diode operated below approximately 15 milliwatts.

The invention further provides a method for detecting individual particles suspended in a fluid using a light detector, the method comprising: generating light; directing the light through an aperture assembly having an inside surface for aperturing the light, an exposed portion of which inside surface is in direct view of the light detector; flowing fluid through the light; collecting light scattered by particles in the flowing fluid using essentially a single optical collection element; preventing substantially all light from the exposed portion of the inside surface from directly illuminating the light detector; and detecting the scattered light to produce a signal characteristic of a parameter of the particles in the flowing fluid, the signal substantially free of any signal due to light reflected from the exposed potion of the inside surface of the aperture assembly. Preferably, the preventing comprises blocking the light reflected from the exposed inside surface of the aperture assembly at or above a critical angle at which the light is capable of being directly detected by the detector. Preferably, the preventing comprises reflecting the light from the inside surface at an angle from the surface that is substantially incapable of directly being detected by the detector. Preferably, the reflecting is accomplished by forming the inside surface of the aperture assembly with a roughness of thirty-two micro-inches or less. Preferably, the reflecting is accomplished by forming the inside surface of the aperture assembly with a roughness of twenty micro-inches or less. Preferably, the reflecting is accomplished by forming the inside surface of the aperture assembly with a roughness of eight micro-inches or less. Preferably, the reflecting is accomplished by molding the inside surface of the aperture assembly in a polished mold. Preferably, the preventing results in the light noise in the signal being reduced to the level of molecular noise. Preferably, the collecting light scattered by particles in the flowing fluid is performed by a single reflector. Preferably, the generating light comprises using a laser with a power of 15 milliwatts or less.

The invention not only provides a reliable, robust, particle counter, but also provides such a particle counter that is capable of significantly more sensitivity than prior art particle counters. The above and other advantages of the present invention may be better understood from a reading of the following description of the preferred exemplary embodiments of the invention taken in conjunction with the drawings in which:

BRIEF DESCRIPTION OF THE DRAWINGS

A more complete understanding of the method and apparatus of the present invention may be obtained by reference to the following Detailed Description when taken in conjunction with the accompanying Drawings wherein:

FIGS. 3A–3E illustrate various views of one embodiment of an aperture tube of an aperture assembly;

DETAILED DESCRIPTION OF THE PRESENT INVENTION

Figure 1:
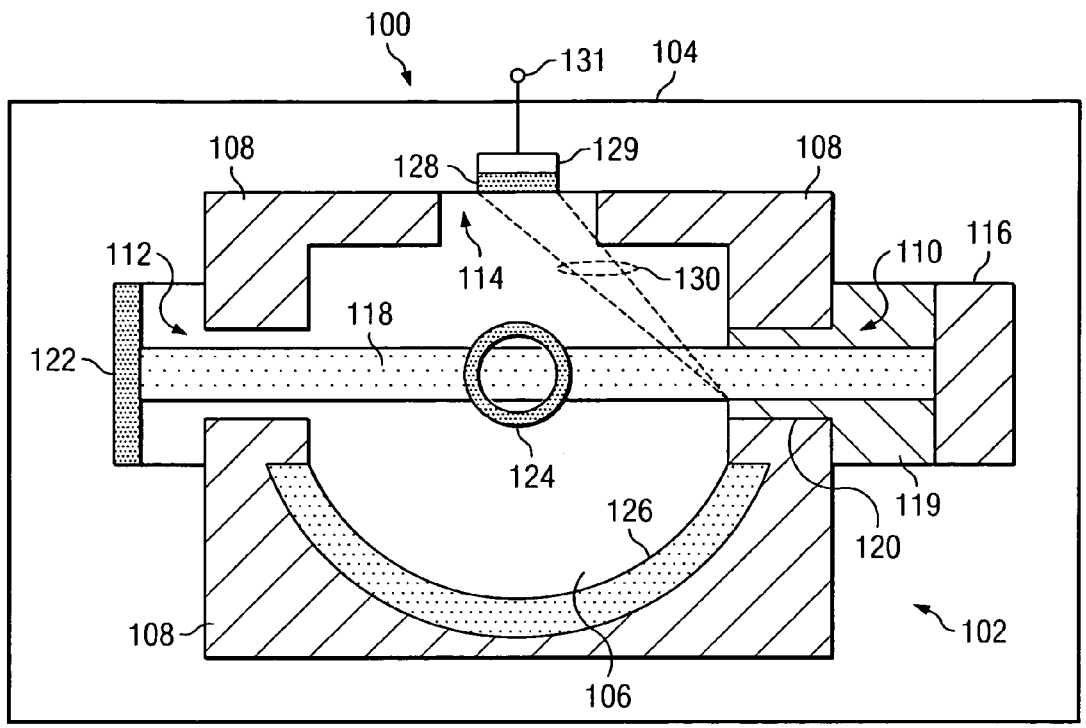
FIG. 1 is a schematic of a particle measurement system including a conventional single component light collecting system.
Figure 2:
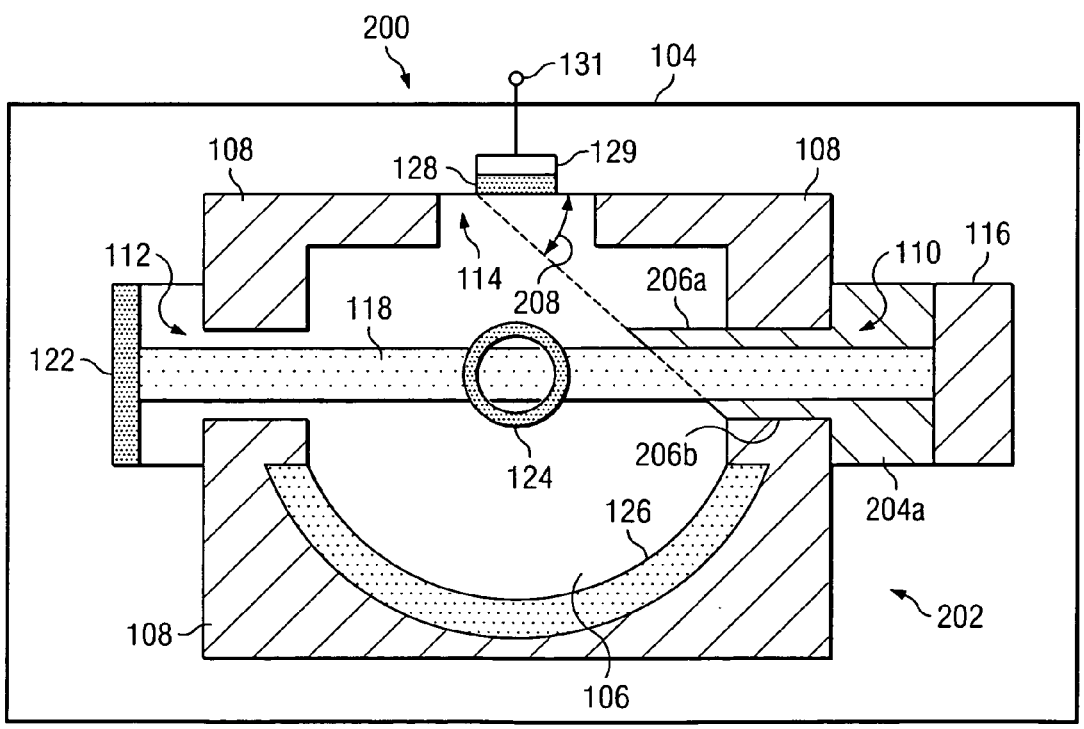
FIG. 2 is a schematic of a particle measurement system including a single component light collecting system according to the principles of the present invention.

FIG. 2 is a schematic of a particle counter or particle measurement system 200 including a single component light collecting system according to the principles of the present invention. As shown, the particle measurement system 200 is composed of many of the same parts as the conventional particle measurement system 100 of FIG. 1. For example, the particle measurement system includes a single component light collecting system 202 that includes sample chamber 106, frame 108, apertures 110, 112, and 114, laser diode module 116, beam stop 122, inlet orifice 124, collecting mirror 126, light detector 128, signal processor/amplifier 129, and output 131. However, the particle measurement system 200 uses alternative components for performing measurement of particles of gas, such as air, to substantially eliminate scattered light noise. For example, the particle measurement system 200 may include an aperture assembly 204a according to the principles of the present invention.

Although the preferred embodiments of the invention utilize a single component light collecting system having opposing apertures 110 and 112, it should be understood that the principles of the present invention may be utilized with a light collecting system with a single aperture. A light stop may be located or mounted to an opposing wall. Still yet, the light stop may be integrated into or engaging the walls of the sample chamber 106. It should be further understood that the principles of the present invention may be utilized in a multi-component light collecting system. The light collecting mirror may be replaced by equivalent structures, such as reflectors, lenses, other optical components, or combination thereof to direct light onto a light detector. Signal processor/amplifier 129 is shown inside housing 200; however, as known in the art, it may also be outside of housing 200. As known in the art, it may take many different forms from a simple amplifier and/or counter to computer. Any conventional amplifier, counter, computer or other equivalent electronics may be used.

The aperture assembly 204a, in the embodiment shown, has a top edge 206a and a bottom edge 206b, where the top edge 206a is configured as a light stop to optically block scattered light produced by spontaneous emission of light from the laser diode module 116 so as to substantially prevent direct illumination of the light detector 128. As shown, the top edge 206a of the aperture assembly 204a extends to a distance where light reflecting from the bottom edge 206b contacts the light detector 128, if at all, at or above a critical angle of the light detector 128. The critical angle 208 is an angle beyond which the light detector 128 is incapable of reacting or detecting light energy. By extending the top edge, scattered light noise is substantially reduced as light energy traveling in any other direction within the sample chamber 106 is absorbed by an optical absorbing surface (e.g., black walls within the sample chamber), thereby preventing the light energy from reaching the light detector. In another embodiment, a beam stop (not shown) may be adapted for coupling to the frame 108 or other structural component within the sample chamber to perform the same or similar light blocking function as an extended top edge of an aperture assembly. In summary, the aperture assembly 204a acts as a self-concealing aperture that is designed to shield its own diffraction and reflection light patterns from direct view of the light detector 128. Using such a configuration may decrease the scattered light noise level of the particle measurement system 200 by greater than a factor of two to be substantially at an electronic noise level.

FIGS. 3A–3E illustrate various views of a component of an aperture assembly 204a. FIG. 3A is an illustration of a perspective view of the aperture assembly 204a. The aperture assembly 204a, which is sometimes called an aperture tube, is composed of a shaft 302 having an outside surface 304 and an inside surface 306. The aperture assembly 204a may further include a head 308 at one end of the shaft 302. The head 308 includes an opening 310 through which a light beam may pass. At the end 312 opposing the head 308 is a top edge 314 and bottom edge 316. The top edge 314 extends beyond the bottom edge 316 relative to the head 308 to operate as a beam stop.

FIG. 3B is a rear view of the aperture assembly 204a. As shown, the head 308 includes an aperture or opening 310 and has a larger diameter than the outside surface 304, shown as a hidden line.

FIG. 3C is a front view of the exemplary aperture assembly 204a. As shown, the head 308 has a larger diameter than the outside surface 304 and inside surface 306, which defines the opening 310 of the aperture assembly 204a. A light beam may thereby pass through the opening 310.

FIG. 3D is a bottom view of the exemplary aperture assembly 204a of FIG. 3A. The top edge 314 extends beyond the bottom edge 316 relative to the head 308. A rim 318 defining the opening 310 to be shaped as an oval is formed by the shaft 304 being cut at an angle. It should be understood that any other geometric shape having a beam stop or overhang is capable of producing the same or similar results.

FIG. 3E is a side view of the exemplary aperture assembly 204a of FIG. 3A. Again, the top edge 314 extends beyond the bottom edge 316 so as to operate as a self-concealing aperture or opening 310 when oriented with the top edge 314 closer to a light detector than the bottom edge 316 to block scattered light noise from directly contacting the light detector.

Figure 4A:
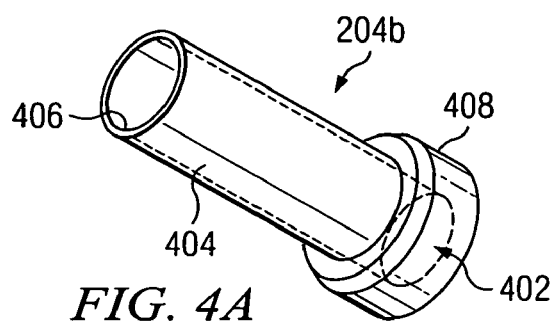
FIGS. 4A–4D illustrate various views of another embodiment of a second embodiment of an aperture tube of an aperture assembly.

FIGS. 4A–4D illustrate various views of another embodiment of a component of an exemplary aperture assembly 204b. FIG. 4A is an illustration of an alternative embodiment of an aperture assembly 204b that may be utilized in accordance with the principles of the present invention. The aperture assembly 204b is configured without a top edge extending beyond a bottom edge. Accordingly, the aperture assembly 204b includes an outside surface 404 and an inside surface 406. As with the aperture assembly 204a, the aperture assembly 204b includes a head 408. Contrary to aperture assemblies utilized in conventional particle measurement systems, the principles of the present invention provide for the inside surface 406 to be smooth and/or glossy. For example, the inside surface 406 may be smooth, polished, composed of a polymer with embedded black colored particles, such as carbon particles, or glossed with a glossy black paint (note that a glossy black paint may be composed of a polymer).

Figure 4B:
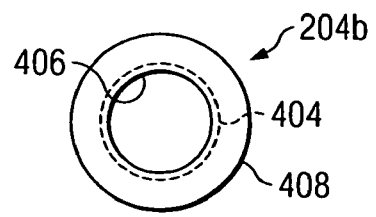

FIG. 4B is an illustration of a rear view of the aperture assembly 204b of FIG. 4A. The head 408 has a larger diameter than the outside surface 404, shown as a hidden line, and inside surface 406. The aperture 402 extends through the head 408 and inside surface 406.

Figure 4C:
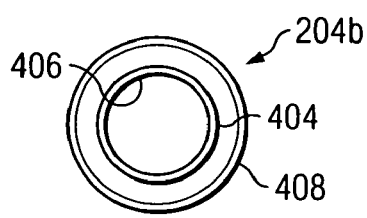

FIG. 4C is an illustration of a front view of the aperture assembly 204b of FIG. 4A. Similar to FIG. 4B, the head 408 has a larger diameter than the outside surface 404.

Figure 4D:
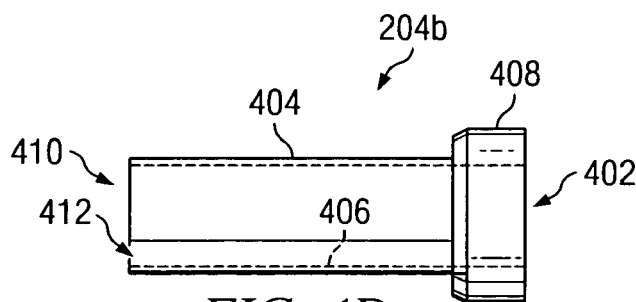

FIG. 4D is an illustration of a side view of the aperture assembly 204b of FIG. 4A. As shown, a front edge 410 of the aperture assembly 204b is substantially flat (i.e., there is no extension portion of a top or bottom edge). Rather than having a physical structure to conceal the aperture 402 of the aperture assembly 204b, the aperture 402 is self-concealed from the light detector 128 (FIG. 2) by the configuration of the inside surface 406 being smooth.

In configuring the inside surface 406 of the aperture assembly 204b, a mechanical ream finish may be utilized on the inside surface 406 such that the roughness of the surface is preferably thirty-two micro inches or less. Roughness refers to the average distance measured from a peak to a neighboring valley. More preferably, the roughness is twenty micro-inches or lower. Most preferably, the roughness is eight micro-inches or less. The finish of the inside surface 406 is highly reflective, such that an incident light has substantially the same reflection angle as incident angle. In one embodiment, the aperture assembly 204b may be composed of a plastic, resin (e.g., Delrin® from DuPont), metal, or glass. In general, using a mechanical ream finish reduces the need for using glossy black paint, urethane, PVC, or other reflective coating, thereby being less expensive. However, a combination of mechanical ream finishing and a glossy coating may also produce desired results. Alternatively, injection molding the aperture 204b using a polished mold may be used to produce a smooth inside surface 406. It should be understood that the aperture assembly 204a may be composed of the same material. In addition, the aperture assembly may be composed of one or more members. Still yet, the aperture assembly preferably has a length at least twice as long as the diameter of the aperture opening to reduce the chances of a spontaneous emitted light beam directly illuminating the light detector.

A polymer, if so used, reflects and absorbs the spontaneous emission light very effectively because the polymer is clear and the light is able to penetrate it. The black color embedded in the polymer absorbs the light. That is, the light tends to get trapped within the polymer and is absorbed by the particles embedded within the polymer. More particularly, because polymer has a very high index of refraction, light enters the polymer and is absorbed by the black color.

In both the embodiment of FIGS. 3A–3E and the embodiment of FIGS. 4A–4D, the aperture assembly 204a or 204b has a portion that is in direct view of the light detecting element 128. However, in each embodiment, the portion that is in direct view of the light detecting element is different. In the embodiment of FIGS. 3A–3E, the portion that is in direct view of the detecting element 128 is the end 312 of the top side of the top edge 314. In the embodiment of FIGS. 4A–4B, the portion that is in direct view of the detecting element 128 is the end 412 of the inside bottom portion of surface 406.

It should be understood that the principles of the present invention may further include a combination of the features of the aperture assemblies 204a and 204b. That is, an aperture assembly may be configured to have an optical blocking mechanism (e.g., beam stop) and smooth and/or glossy inside surface. By utilizing both features, the scattered light noise may be reduced even further than adopting either one or the other. However, the use of the smooth and/or glossy inside surface 406 reduces the scattered noise level at or below the molecular noise level.

Figure 5:
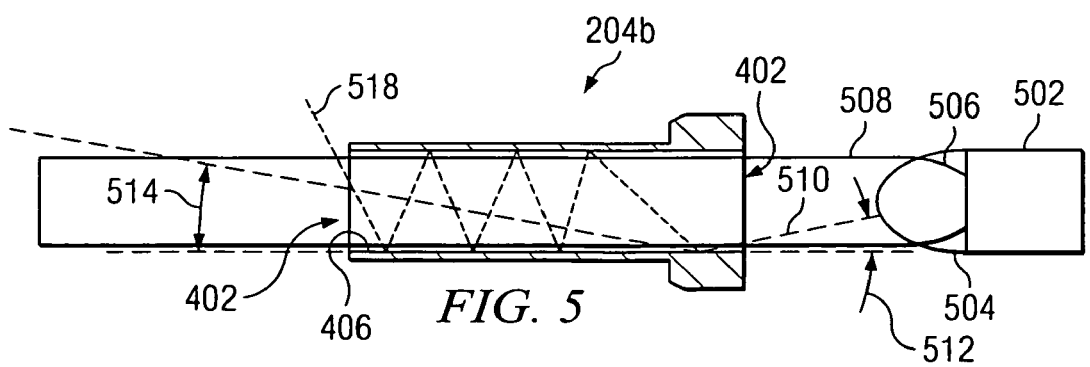
FIG. 5 is a schematic of the aperture tube of FIG. 4D showing a ray trace of a spontaneous emission of light reflecting from an inside surface of the aperture tube.

FIG. 5 is a schematic of a side view of the aperture assembly 204b of FIG. 4D showing a ray trace of a spontaneous emission of light passing therethrough. As shown, a light emitting diode 502 having a lens 504 collimates light 506 generated by the LED 502 into a light beam 508. The light beam 508 is collimated and passes through the aperture 402 of the aperture assembly 204b. A spontaneous emission light beam 510 resulting from a spontaneous emission of light is incident at a point 512 of the inside surface 406. Because of the smoothness of the inside surface 406, the spontaneous emission light beam 510 reflects from the inside surface 406 at a reflection angle 514 that is substantially the same as an incident angle 512. To contrast with conventional techniques for reducing scattered light noise, light beam 518 results from conventional techniques for preparing the inside surface 406 to cause high angles of reflection within the aperture assembly 204b. The high angles of reflection of conventional aperture assemblies, however, result in the light beam, albeit at a lower power, directly contacting the light detector 128 (FIG. 1) when exiting the aperture 402 of the aperture assembly 204b.

The results of utilizing the principles of the present invention, either using the configuration of the aperture assembly 204a or 204b, is that scattered light noise is essentially eliminated in a particle measurement system using a single component light collecting system as shown in FIG. 2. In fact, utilizing the principles of the present invention at higher laser powers may reduce the level of scattered light noise to the point that the particle measurement system detects noise that is at the background level related to molecular motion (i.e., molecular noise).

Because the scattered light noise is substantially eliminated, a signal-to-noise level equivalent to or better than that of conventional particle measurement systems may be obtained with less laser power. Conventional, low-cost particle measurement systems typically utilize twenty milliwatts (mW) for driving the laser diode used as a light source. Utilizing the principles of the present invention, the laser diode may be powered with fifteen mW or lower and have the same or better signal-to-noise ratio. The life extension of a laser diode is proportional to (power derate divided by power full)$^{-2.7}$, where power derate is the actual power at which the laser is run and full power is the full power of the laser diode. The power difference results in the laser of the particle counter having a lifetime that is approximately four times as long as those of conventional particle measurement systems.

The previous description is of preferred embodiments for implementing the invention, and the scope of the invention should not necessarily be limited by this description. The scope of the present invention is instead defined by the following claims.

We claim:

1. A system for detecting individual particles suspended in a fluid, said system comprising:
    a housing having a sample chamber;
    a fluid inlet orifice directing a fluid flow into said sample chamber;
    a light source for producing and directing light into said sample chamber and through said fluid flow;
    a light detecting element producing an output signal characteristic of individual particles suspended in said fluid;
    an aperture assembly located to aperture said light, said aperture assembly having a portion in direct view of said light detecting element, said aperture assembly having an inside surface exposed to said light and a first end in said sample chamber; and
    a light collector located to collect light scattered by particles in said fluid flow and direct said collected light to said light detecting element; the optical components of said light collector consisting essentially of a single optical component;
    said inside surface of said aperture assembly configured to reflect light so that essentially none of said light reflected from said inside surface is capable of directly illuminating said light detector, thereby reducing optical noise in the system for detecting particles.

2. The system according to claim 1 wherein said inside surface of said aperture assembly has a mechanical ream finish.

3. The system according to claim 1 wherein said inside surface of said aperture assembly has a maximum roughness of thirty-two micro-inches or less.

4. The system according to claim 1 wherein said inside surface of said aperture assembly has a maximum roughness of twenty micro-inches or less.

5. The system according to claim 1 wherein said inside surface of said aperture assembly has a maximum roughness of eight micro-inches or less.

6. The system according to claim 1 wherein said inside surface of said aperture assembly comprises a polymer.

7. The system according to claim 6 wherein said polymer is embedded with black colored particles.

8. The system according to claim 1 wherein said inside surface of said aperture assembly is covered with a glossy black paint.

9. The system according to claim 1 wherein said inside surface of said aperture assembly is molded using a polished mold.

10. The system according to claim 1 wherein said aperture assembly has a length at least twice as long as the diameter of the aperture opening.

11. The system according to claim 1 wherein said light source is a laser diode operated below approximately 15 milliwatts.

12. A method for detecting individual particles suspended in a fluid using a light detector, said method comprising:
   generating light;
   directing said light through an aperture assembly having an inside surface for aperturing said light, an exposed portion of which inside surface is in direct view of said light detector;
   flowing fluid through said light;
   collecting light scattered by particles in said flowing fluid using essentially a single optical collection element;
   preventing substantially all light from said exposed portion of said inside surface from directly illuminating said light detector; and
   detecting said scattered light to produce a signal characteristic of a parameter of said particles in said flowing fluid, said signal substantially free of any signal due to light reflected from said exposed potion of said inside surface of said aperture assembly.

13. The method according to claim 12 wherein said preventing comprises blocking the light reflected from said exposed inside surface of said aperture assembly at or above a critical angle at which the light is capable of being directly detected by said detector.

14. The method according to claim 12 wherein said preventing comprises reflecting the light from said inside surface at an angle from the said surface that is substantially incapable of directly being detected by said detector.

15. The method according to claim 14 wherein said reflecting is accomplished by forming said inside surface of said aperture assembly with a roughness of thirty-two microinches or less.

16. The method according to claim 14 wherein said reflecting is accomplished by forming said inside surface of said aperture assembly with a roughness of twenty microinches or less.

17. The method according to claim 14 wherein said reflecting is accomplished by forming said inside surface of said aperture assembly with a roughness of eight microinches or less.

18. The method according to claim 14 wherein said reflecting is accomplished by molding said inside surface of said aperture assembly in a polished mold.

19. The method according to claim 12 wherein said preventing results in the light noise in said signal being reduced to a level of molecular noise.

20. The method according to claim 12 wherein said collecting light scattered by particles in said flowing fluid is performed by a single reflector.

21. The method according to claim 12 wherein said generating light comprises using a laser with a power of 15 milliwatts or less.

* * * * *